United States Patent [19]

Kim et al.

[11] Patent Number: 5,306,722
[45] Date of Patent: Apr. 26, 1994

[54] THYMIDINE DERIVATIVES AND THERAPEUTIC METHOD OF USE

[75] Inventors: Choung U. Kim, Madison; Bing Y. Luh, Killingworth; Peter F. Misco, Durham, all of Conn.

[73] Assignee: Bristol-Myers Squibb Company, New York, N.Y.

[21] Appl. No.: 939,232

[22] Filed: Sep. 2, 1992

[51] Int. Cl.$^5$ .................. A61K 31/505; C07D 403/04
[52] U.S. Cl. .................................... 514/274; 544/310; 514/269
[58] Field of Search ........................... 536/28.54, 28.2; 514/49, 50, 269, 258, 256, 274; 544/310, 242, 224

[56] References Cited

U.S. PATENT DOCUMENTS

| | | | |
|---|---|---|---|
| 4,782,062 | 11/1988 | Tolman et al. | 514/262 |
| 4,851,519 | 7/1989 | Lambert et al. | 536/28.2 |
| 4,863,927 | 9/1989 | Tolman et al. | 514/274 |
| 4,882,316 | 11/1989 | Lambert et al. | 514/49 |
| 4,886,785 | 12/1989 | Lambert et al. | 514/50 |
| 5,008,252 | 4/1991 | Cheng et al. | 514/50 |
| 5,091,375 | 2/1992 | Hector et al. | 514/50 |

FOREIGN PATENT DOCUMENTS

| | | | |
|---|---|---|---|
| 147775 | 4/1981 | Fed. Rep. of Germany | 536/28.53 |
| 56-99478 | 8/1981 | Japan | 536/28.55 |

OTHER PUBLICATIONS

Iain S. Sim et al, "Inhibition of Herpes Simplex Virus Thymidine Kinase by 5'-Substituted Thymidine Analogues. Comparison of the Types 1 and 2 Enzymes," *Nucleosides and Nucleotides*, 1988, 7(2), pp. 129–135.

Louise M. Nutter et al, "Demonstration of Viral Thymidine Kinase Inhibitor and Its Effect on Deoxynucleotide Metabolism in Cells Infected with Herpes Simplex Virus," *Antimicrobial Agents and Chemotherapy*, Mar. 1987, vol. 31, No. 3, pp. 368–374.

Federico Focher et al, "N$^2$-Phenyldeoxyguanosine: A Novel Selective Inhibitor of Herpes Simplex Thymidine Kinase," *Journal of Medicinal Chemistry*, 1988, 31, pp. 1496–1500.

Catherine Hildebrand et al, "Structure-Activity Relationships of N$^2$-Substituted Guanines as Inhibitors of HSV1 and HSV2 Thymidine Kinases," *Journal of Medicinal Chemistry*, 1930, 33, pp. 203–206.

H. E. Kaufman et al, "Suppression of Ocular Herpes Recurrences by a Thymidine Kinase Inhibitor in Squirrel Monkeys," *Antiviral Research*, 1991, 16, pp. 227–232.

J. A. Martin et al, "New Potent and Selective Inhibitors of Herpes Simplex Virus Thymidine Kinase," *Nucleosides and Nucleotides*, 1989, 8(5&6), pp. 753–764.

J. A. Martin et al, "Design of Inhibitors of Herpes Simplex Virus Thymidine Kinase," *American Chemical Society Symposium Proceedings*, 1989, 401:103–115.

CA 115 (19):208461b (1991) Kim.

*Primary Examiner*—Johnnie R. Brown
*Assistant Examiner*—A. Varma
*Attorney, Agent, or Firm*—William T. Han

[57] ABSTRACT

Thymidine kinase inhibitor of formula I

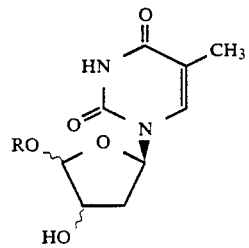

in which R is $C_{1-6}$alkyl or $AR(CH_2)_n$—, wherein Ar represents phenyl optionally substituted with one to five same or different halogen, $C_{1-6}$ alkyl or $C_{1-6}$ alkyloxy; and n equals one to six.

A further aspect of the present invention provides a method of inhibiting viral thymidine kinase. Yet another aspect of the invention relates to treating herpes simplex viral infections in mammals. Yet another aspect of the invention provides a pharmaceutical formulation.

21 Claims, No Drawings

THYMIDINE DERIVATIVES AND THERAPEUTIC METHOD OF USE

BACKGROUND OF INVENTION

This invention relates to inhibitors of viral thymidine kinases.

Herpes simplex viruses type (HSV-1) and type 2 (HSV-2) induce unique virus-specified thymidine kinases (dthd kinase) in infected cells. While the activity of viral dthd kinase does not appear to be critical for virus replication in cell culture systems, studies have suggested that it is important for virus pathogenicity and reactiviation of latent virus from neural cells. Nutter et al., *Demonstration of Viral Thymidine Kinase Inhibitor and Its Effect on Dexoynucleotide Metabolism in Cells Infected with Hempers Simplex Virus*, Antimicrobial Agents and Chemotherapy, Vol 31, No. 3, pp d368-374 (1987). Thus it is the intention of this invention to provide novel thymidine kinase inhibitors for antiviral agents in mammals.

SUMMARY OF INVENTION

This invention relates to a compound of formula I

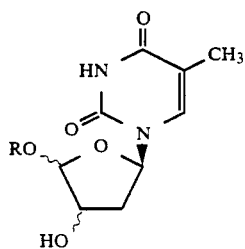

in which R is $C_{1-6}$alkyl or $Ar(CH_2)_n$—, wherein Ar represents phenyl optionally substituted with one to five same or different halogen, $C_{1-6}$ alkyl or $C_{1-6}$ alkyloxy; n is one to six.

A further aspect of the present invention provides a method for inhibiting viral thymidine kinases with a compound of formula I.

Yet another aspect of the invention relates to a method for treating a mammal afflicted with herpes simplex viral infection which comprises administering to said mammal a compound of formula I.

Yet another aspect of the invention provides a pharmaceutical formulation comprising a compound of formula I and one or more pharmaceutically acceptable carriers, excipients or diluents.

DETAILED DESCRIPTION OF INVENTION

As used herein, $C_{1-6}$ alkyl refers to straight and branched chain alkyl groups with one to six carbon atoms, and such groups include methyl, ethyl, n-propyl, isopropyl, n-butyl, t-butyl, n-pentyl, n-hexyl, 3-methylpentyl, or the like alkyl groups; $C_{1-6}$ alkyloxy (alkoxy) refers to straight or branched alkyloxy groups such as methoxy, ethoxy, n-propoxy, i-propoxy, n-butoxy, t-butoxy, n-pentyloxy, n-hexyloxy, or 3-methylpentyloxy, to name a few.

The specific example which follows illustrate the synthesis of representative compounds of the instant invention and are not to be construed as limiting the invention in sphere or scope. The methods may be adapted to variations in order to produce compounds embraced by this invention but not specifically disclosed. Further, variations of the methods to produce the same compounds in somewhat different fashion will also be evident to one skilled in the art.

The nuclear magnetic resonance (NMR) spectral characteristics refer to chemical shifts ($\delta$) expressed in parts per million (ppm) versus tetramethylsilane (TMS) as reference standard. The nature of the shifts as to multiplicity is reported as broad singlet (bs), broad doublet (bd), broad triplet (bt), broad quartet (bq), singlet (s), multiplet (m), doublet (d), quartet (q), triplet (t), doublet of doublet (dd), doublet of triplet (dt), and doublet of quartet (dq).

Synthesis of (2R, 4S, 5S)-1-(Tetrahydro-4-hydroxy-5-methoxy-2-furanyl) thymine (2) and (2R, 4R, 5R)-1-(Tetrahydro-4-hydroxy-5-methoxy-2-furanyl)thymine (3)

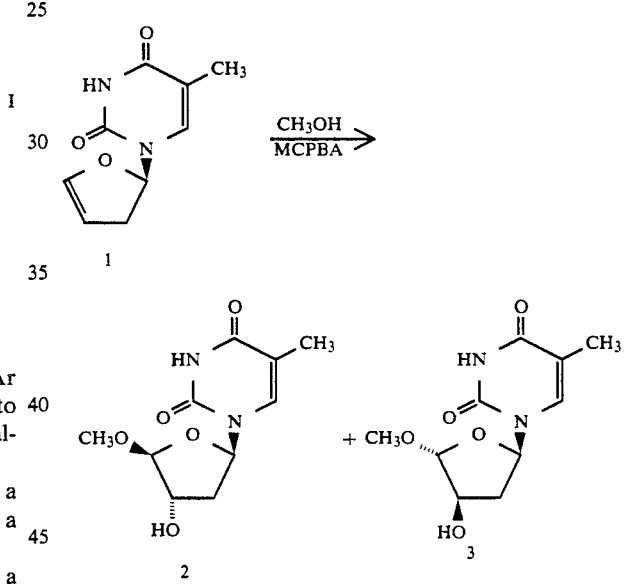

To a solution of glycal 1 (1.94 g, 10 mmol) prepared according to the literature procedures: J. Zemlicka, et al., *J. Amer. Chem. Soc.*, 94 3213 (1972)] in MeOH (4 mL) and $CH_2Cl_2$ (5 mL) at 0° C. was added dropwise a solution of 3-chloroperbenzoic acid (80–85%, ca. 11 mmol) in $CH_2Cl_2$ (2 mL) under nitrogen. After being stirred at room temperature for 1.5 h, the mixture was diluted with $CH_2Cl_2$ and aqueous $NAHCO_3$. The organic phase was washed with brine, dried over $MgSO_4$, and concentrated in vacuo. The residual oil was chromatographed on silica gel using 5% MEOH in $CH_2Cl_2$ as eluent to separate the mixture of 2 and 3. The isomer 3 was eluted first and obtained as amorphous solid (1.25 g, 55%). Continuing the column with 5% MeOH in $CH_2Cl_2$, the isomer 2 was isolated as a fine residue (yield: 350 mg, 15%). In a similar manner as described here, compounds 4–15 were prepared using the corresponding alcohols; their physical and spectroscopic data are summarized in Table 1.

TABLE 1

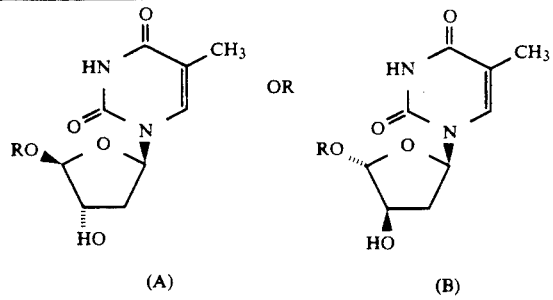

| Compound | Isomer | Yield % | MP (°C.) | H-2 | H-4 | H-5 |
|---|---|---|---|---|---|---|
| 2 (R = CH₃) | A | 15 | 202 | 6.43 (t, J=6.6 Hz) | 4.12 (s, bs) | 5.41 (d, J=3.9 Hz) |
| 3 (R = CH₃) | B | 55 | 150 | 6.12 (dd, J=6.8, 1.0 Hz) | 4.25 (d, J=4.9 Hz) | 5.26 (s) |
| 4 (R = CH₂CH₃) | A | 12 | 232 | 6.43 (t, J=6.9 Hz) | 4.13 (s, bs) | 5.42 (d, J=3.9 Hz) |
| 5 (R = CH₂CH₃) | B | 45 | 170 | 6.13 (dd, J=7.0, 1.3 Hz) | 4.29 (d, J=4.8 Hz) | 5.25 (s) |
| 6 (R = CH₂CH₂CH₃) | A | 11 | 175 | 6.52 (t, J=7.1 Hz) | 4.26 (d, J=4.1 Hz) | 4.95 (s) |
| 7 (R = CH₂CH₂CH₃) | B | 48 | 120 | 6.29 (dd, J=8.1, 2.4 Hz) | 4.20 (d, J=5.4 Hz) | 5.13 (s) |
| 8 (R = t-Bu) | A | 5 | 177 | 6.34 (t, J=6.7 Hz) | 3.99 (d, J=3.9 Hz) | 5.15 (s) |
| 9 (R = t-Bu) | B | 37 | 115 | 6.13 (d, J=6.9 Hz) | 4.18 (d, J=4.3 Hz) | 5.27 (s) |
| 10 (R = CH₂Ph) | A | 9 | 174 | 6.75 (t, J=6.5 Hz) | 4.46 (t, J=4.5 Hz) | 5.11 (s) |
| 11 (R = CH₂Ph) | B | 31 | 130 | 6.23 (d, J=7.6 Hz) | 4.35 (d, J=4.6 Hz) | 5.28 (s) |
| 12 (R = CH₂CH₂Ph) | A | 12 | 175 | 6.56 (t, J=6.7 Hz) | 4.24 (d, J=4.4 Hz) | 4.96 (s) |
| 13 (R = CH₂CH₂Ph) | B | 49 | 65 | 6.12 (dd, J=8.0, 2.1 Hz) | 4.26 (d, J=5.4 Hz) | 5.14 (s) |
| 14 (R = CH₂CH₂CH₂Ph) | A | 12 | 115 | 6.58 (t, J=6.7 Hz) | 4.28 (d, J=4.1 Hz) | 4.93 (s) |
| 15 (R = CH₂CH₂CH₂Ph) | B | 49 | 70 | 6.28 (dd, J=8.3, 2.4 Hz) | 4.20 (d, J=5.2 Hz) | 5.12 (s) |
| 16 (R = p-bromophenymethyl) | B | 9 | 185 | 6.27 (dd, J=6.7, 1.0 Hz) | 4.35 (d, J=4.7 Hz) | 5.29 (s) |

$^a$CDCl₃, 300 MHz

THYMIDINE KINASE INHIBITORY ASSAY

Table 2 lists results of thymidine kinase inhibitory assay.

The reaction (50 μl) was performed in: 50 mM Tris-HCl pH 7.5, 5 mM MgCl₂, 30 mM KCl, 2 mM dithiothreitol, 5 mM ATP, 1 μM [³H]thymidine, 0-20 μM potential inhibitor, 0.075 mg/ml bovine serum albumin, 0.1 unit/ml HSV-1 TK. Incubation was at 37° C. for 1 hour. Samples (40 μl) were spotted on DE-81 filter disks, washed with 1 mM ammonium formate (pH 7), three times with water, twice with ethanol, and dried. Radioactivity was quantitated in a scintillation counter.

TK (thymidine kinase) was affinity purified from HSV-1 (KOS) infected cells by published procedures (Fyfe (1982) Mol. Pharmacol. 21:432-437 and Field et al. (1990) Antiviral Res. 13:41-52). One unit is defined as 1 nanomole thymidine phosphorylated per hour.

In Table 2, inhibition constants were determined from slope replots (1/slope vs [I]) of Lineweaver-Burk plots. "N" indicates the number of experiments, and each experiment was done in triplicate.

TABLE 2

| Compound | $K_i$, μM | |
|---|---|---|
| 2 | 3.2 ± 0.3 | (N = 4) |
| 13 | 4.3 ± 1.8 | (N = 3) |
| 16 | 10.1 ± 4.7 | (N = 3) |
| 12 | 26 | (N = 1) |

The foregoing test shows that compounds of formula I are useful for inhibiting viral thymidine kinases. The compounds of formula I can also be administered for the control or prevention of viral infection, such as herpes simplex viral infections, to mammals in need of such treatment. The compounds of formula I can also be used as medicaments in the form of pharmaceutical preparations (formulations) which contain them in association with a compatible pharmaceutical carrier material. This can be an organic or inorganic carrier suitable for enteral, e.g., oral, or parenteral administration. Examples of such carriers are water, gelatine, gum arabic, lactose, starch, magnesium stearate, talc, vegetable oils, polyalkylene glycols and petroleum jelly. The pharmaceutical preparations can be made up in a solid form, e.g., as tablets, dragees, suppositories or capsules, or in a liquid form, e.g. as solutions, suspensions or emulsions; they may be subjected to standard pharmaceutical operations, e.g. sterilization and/or may contain adjuvants, e.g. preserving, stabilizing, wetting or emulsifying agents, salts for varying the osmotic pressure or buffers. They may also contain other therapeutically valuable substances.

The compounds of formula I can be administered to adult humans in a daily dosage of from about 1 to 1000 mg, preferably about 5 to 500 mg. The daily dosage may be administered as a single dose or in divided doses. The above dosage range is given by way of example only and can be varied upwards or downwards depending on factors such as the particular compound being administered, the route of administration, the severity of the indication being treated and the condition of the patient.

The following Example illustrates a pharmaceutical preparation containing a compound of formula I:

Tablets may contain the following ingredients:

| Ingredient | Per tablet |
|---|---|
| Compound of formula I | 100 mg |
| Lactose | 70 mg |
| Maize starch | 70 mg |
| Polyvinylpyrrolidone | 5 mg |
| Magnesium stearate | 5 mg |
| Tablet weight | 250 mg |

What is claimed is:

1. A compound of formula I

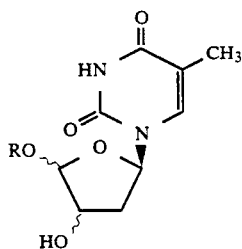

in which R is $C_{1-6}$alkyl or $Ar(CH_2)_n-$, wherein Ar represents phenyl optionally substituted with one to five same or different halogen, $C_{1-6}$ alkyl or $C_{1-6}$ alkyloxy; and n equals one to six.

2. A compound of claim 1, wherein R is as defined in claim 1 which has the formula

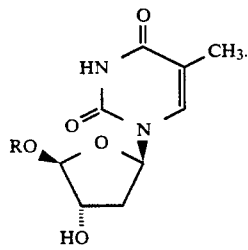

3. The compound of claim 2 in which R is methyl.
4. The compound of claim 2 in which R is ethyl.
5. The compound of claim 2 in which R is n-propyl.
6. The compound of claim 2 in which R is t-butyl.
7. The compound of claim 2 in which R is phenylmethyl.
8. The compound of claim 2 in which R is 2-phenylethyl.
9. The compound of claim 2 in which R is 3-phenylproypyl.
10. The compound of claim 2 in which R is 4-bromophenylmethyl.
11. A compound of claim 1, wherein R is as defined in claim 1 which has the formula

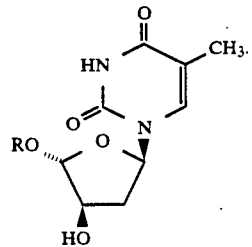

12. The compound of claim 11 in which R is methyl.
13. The compound of claim 11 in which R is ethyl.
14. The compound of claim 11 in which R is n-propyl.
15. The compound of claim 11 in which R is t-butyl.
16. The compound of claim 11 in which R is phenylmethyl.
17. The compound of claim 11 in which R is 2-phenylethyl.
18. The compound of claim 11 in which R is 3-phenylproypyl.
19. The compound of claim 11 in which R is 4-bromophenylmethyl.
20. A pharmaceutical formulation which comprises as an active ingredient a compound as claimed in any one of claims 1 to 19, or a pharmaceutically acceptable salt thereof, associated with one or more pharmaceutically acceptable carriers, excipients or diluents therefore.
21. A method of inhibiting viral thymidine kinase with a compound as claimed in any one of claims 1 to 19.

* * * * *